US009956235B2

(12) United States Patent
Mayer et al.

(10) Patent No.: US 9,956,235 B2
(45) Date of Patent: May 1, 2018

(54) REDUCING THE REPRODUCTIVE CAPACITY OF MAMMALS

(71) Applicant: SENESTECH, INC., Flagstaff, AZ (US)

(72) Inventors: Lorretta P. Mayer, Flagstaff, AZ (US); Cheryl A. Dyer, Flagstaff, AZ (US)

(73) Assignee: SENESTECH, INC., Flagstaff, AZ (US)

( * ) Notice: Subject to any disclaimer, the term of this patent is extended or adjusted under 35 U.S.C. 154(b) by 0 days. days.

(21) Appl. No.: 14/423,245

(22) PCT Filed: Aug. 23, 2013

(86) PCT No.: PCT/US2013/056428
§ 371 (c)(1),
(2) Date: Feb. 23, 2015

(87) PCT Pub. No.: WO2014/031979
PCT Pub. Date: Feb. 27, 2014

(65) Prior Publication Data
US 2015/0224124 A1  Aug. 13, 2015

Related U.S. Application Data

(60) Provisional application No. 61/692,624, filed on Aug. 23, 2012.

(51) Int. Cl.
*A61K 31/336* (2006.01)
*A61K 31/343* (2006.01)
*A61K 31/665* (2006.01)
*A61K 31/585* (2006.01)

(52) U.S. Cl.
CPC .......... *A61K 31/665* (2013.01); *A61K 31/336* (2013.01); *A61K 31/343* (2013.01); *A61K 31/585* (2013.01); *A01K 2207/20* (2013.01)

(58) Field of Classification Search
CPC . A01K 2207/20; A61K 31/336; A61K 31/343
See application file for complete search history.

(56) References Cited

U.S. PATENT DOCUMENTS

| | | |
|---|---|---|
| 6,004,999 A | 12/1999 | Jung et al. |
| 6,150,539 A | 11/2000 | Musser |
| 6,294,546 B1 | 9/2001 | Rosen et al. |
| 6,548,537 B1 | 4/2003 | Dai et al. |
| 7,626,044 B2 | 12/2009 | Li et al. |
| 8,268,882 B2 | 9/2012 | Musesr |
| 2004/0073962 A1 | 4/2004 | Hoyer et al. |
| 2010/0056624 A1* | 3/2010 | Hoyer ................ G01N 33/5088 514/475 |

FOREIGN PATENT DOCUMENTS

| | | |
|---|---|---|
| JP | 2001-504437 A | 4/2001 |
| WO | WO 02/09698 A1 | 2/2002 |
| WO | WO 2004/019676 A2 | 3/2004 |
| WO | 2010/051498 | 5/2010 |
| WO | WO 2010/051498 | 5/2010 |
| WO | 2010/129918 | 11/2010 |
| WO | WO 2010/129918 | 11/2010 |
| WO | WO 2014/031979 | 2/2014 |

OTHER PUBLICATIONS

Xu et al. (African Journal of Pharmacy and Pharmacology vol. 4(6). pp. 422-430, Jun. 2010).*
Hendry et al. (Brit. J. Pharmacol., 1951, 6, p. 235-255).*
Knipling et al. (Potential role of sterilization for suppressing rat populations. (1972) Technical Bulletin No. 1455, US Department of Agriculture, Agricultural Research Service, Maryland, pp. 1-27).*
Rose et al. (Nature, 165, p. 993-996 (Jun. 24, 1950)).*
International Search Report dated Jan. 24, 2014 in PCT/US13/056428 filed Aug. 23, 2013.
Liu, J. et al., "Triptolide induces adverse effect on reproductive parameters of female Sprague-Dawley rats", Drug and Chemical Toxicology, vol. 34, No. 1, (8 Pages), 2010.
Leuenroth, S. et al., "Triptolide is a traditional Chinese medicine-derived inhibitor of polycystic kidney disease ", PNAS, vol. 104, No. 11, pp. 4389-4394, 2007.
Patil, S. P., "A preclinical development of a novel triptolide prodrug for cancer treatment ", University of Minnesota, Jan. 2011[online], [retrieved on Dec. 26, 2013], Retrieved from the internet <URL:http://www.docin.com/p-318003236.html>; p. iv, paragraph 2; p. v, paragraph 3; p. 3, POM prodrug formula (4 Pages).
B. Van Duuren, "Carcinogenic Epoxides, Lactones, and Halo-Ethers and Their Mode of Action", Laboratory of Organic Chemistry and Carcinogenesis, Institute of Environmental Medicine, pp. 633-651.
C. Weil, et al., "Experimental Carcinogenicity and Acute Toxicity of Representative Epoxides", Industrial Hygiene Journal, 1963, pp. 305-325.
B. Van Duuren, et al., "Carcinogenicity of Epoxides, Lactones, and Peroxy Compounds. VI. Structure and Carcinogenic Activity", Journal of The National Cancer Institute, vol. 39, 1967, pp. 1217-1228.
B. Van Duuren, et al., "Carcinogenicity of Epoxides, Lactones, and Peroxy Compounds. V. Subcutaneous Injection in Rats", Journal of The National Cancer Institute, vol. 39, 1967, pp. 1213-1216.
B. Van Duuren, et al., "Carcinogenicity of Epoxides, Lactones, and Peroxy Compounds. IV. Tumor Response in Epithellal and Connective Tissue in Mice and Rats", Journal of The National Cancer Institute, vol. 37, 1966, pp. 825-838.
B. Van Duuren, et al., "Carcinogenicity of Epoxides, Lactones, and Peroxy Compounds", Journal of The National Cancer Institute, vol. 31, 1963, pp. 41-55.
B. Van Duuren, et al., "Carcinogenicity of Epoxides, Lactones, and Peroxy Compounds. Part II[1,2,3]", Journal of The National Cancer Institute, vol. 35, 1965, pp. 707-717.

(Continued)

*Primary Examiner* — Robert Halvin
(74) *Attorney, Agent, or Firm* — Oblon, McClelland, Maier & Neustadt, L.L.P.

(57) ABSTRACT

Provided are compositions and methods for reducing the reproductive capacity of mammals. The compositions and methods involve the use and administration of (a) a diterpenoid epoxide comprising a triptolide skeleton and which causes ovarian follicle depletion in female mammals and (b) an organic diepoxide which causes ovarian follicle depletion in female mammals.

17 Claims, 16 Drawing Sheets

(56) References Cited

OTHER PUBLICATIONS

J. Liu, et al., "Triptolide Induces Adverse Effect on Reproductive Parameters of Female Sprague-Dawley Rats", Drug and Chemical Toxicology, vol. 34, No. 1, 2010, pp. 1-7.
S. Leuenroth, et al., "Triptolide is a Traditional Chinese Medicine-Derived Inhibitor of Polycystic Kidney Disease", PNAS, vol. 104, No. 11, Mar. 13, 2007, pp. 4389-4394.
S. Patil, "Preclinical Development of a Novel Triptolide Prodrug for Cancer Treatment", http://www.docin.com/p-318003236.html.
Huynh et al., Journal of Andrology, 2000, vol. 21, No. 5, pp. 689-699.
Hakim et al., Journal of Andrology, 2000, vol. 21, No. 3, pp. 431-437.
Communication pursuant to Rules 70(2) and 70a(2) EPC dated Mar. 8, 2016 in European Patent Application 13831276.4.
Extended European Search Report dated Feb. 18, 2016 in Patent Application No. 13831276.4.
Russian Office Action in corresponding Application No. 2015110047/15, dated Oct. 31, 2016. (w/English Translation).
Brandy Pyzyna, et al., "Liquid Fertility Management Bait Uptake by Urban Rats within New York City Subway Refuse Rooms", National Wildlife Management Centre, Animal Health and Veterinary Laboratories Agency, Sand Hutton, York, UK, Published at Univ. of Calif., Davis. 2014, pp. 375-379.
Office Action dated Feb. 28, 2017 in Japanese Patent Application No. 2015-528693 (with English language translation).

\* cited by examiner

REDUCING THE REPRODUCTIVE CAPACITY OF MAMMALS

CONTINUING APPLICATION INFORMATION

This application claims benefit of U.S. Provisional Application Ser. No. 61/692,624, filed on Aug. 23, 2012, and incorporated herein by reference.

BACKGROUND OF THE INVENTION

Field of the Invention

The present invention relates to compositions and methods for reducing the reproductive capacity of mammals. The compositions and methods involve the use and administration of (a) a diterpenoid epoxide comprising a triptolide skeleton and which causes ovarian follicle depletion in female mammals in combination with (b) an organic diepoxide which causes ovarian follicle depletion in female mammals.

Description of the Background

Compositions that reduce the reproductive capacity of mammals, particularly those which induce ovarian follicle depletion, may be desirable for a variety of reasons. Such compositions may be used to induce infertility in pests, such as rodents, to control the population of the pests, and to produce animal models for study. For example, animals, such as rats, with induced follicle depletion can be used to create animal models that can be used to study menopause in and its effects on other animals, such as humans.

Rodent pests are a major cause of damage to the world's agricultural crops and food stores. Rodents eat and contaminate food supplies, carry diseases, damage infrastructure, and can disrupt indigenous wildlife and ecosystems. For decades, rodenticides have been used to try to control rodent populations, yet, to date, rodent populations prove difficult to control and rodent damage is widespread. One reason that rodent populations are difficult to control is that rodents tend to have relatively short gestation periods (e.g., on the order of a few weeks), and thus, unless the entire population is eliminated, the population can restore itself once the rodenticide is exhausted or depleted. In addition, poisons may not specifically target the pests and may affect other animals, including humans. Thus, the use of pesticides may be tempered by other environmental concerns.

The rate of rat reproduction is tied to the quantity of food available and the quality of food sources. Thus, while poisoning reduces the population, it also reduces competition for food, so survivors' reproduction may go unchecked.

A promising alternative to using rodenticides involves using formulations that accelerate ovarian follicle depletion to manage populations of rodent pests via fertility control. The epoxide 4-vinylcyclohexene diepoxide (VCD) has been efficacious to cause non-regenerating primordial follicle depletion in Sprague Dawley rats (*Rattus norvegicus*) via gavage. However, to be effective for population management, it is desirable to target multiple, e.g., all, ovarian follicles for depletion, so to have an immediate impact on fertility and pup production. Accordingly, improved compositions that induce ovarian follicle depletion at multiple stages and methods of using the composition are desired.

SUMMARY OF THE INVENTION

It is an object of the present invention to provide a composition which can be used to reduce the reproductive capacity of mammals. In particular, the compositions of the present invention induce ovarian follicle depletion when administered to female mammals as well as male mammals. It is another object of the present invention to provide methods of reducing the population of mammals with the compositions of the present invention.

The objects of the present invention may be accomplished with a composition suitable for depleting ovarian follicles in female mammals, comprising:

(a) a diterpenoid epoxide comprising a triptolide skeleton and which causes ovarian follicle depletion in female mammals, and (b) an organic diepoxide which causes ovarian follicle depletion in female mammals.

In a preferred embodiment of the invention, the diterpenoid epoxide comprising a triptolide skeleton (a) is represented by the formula:

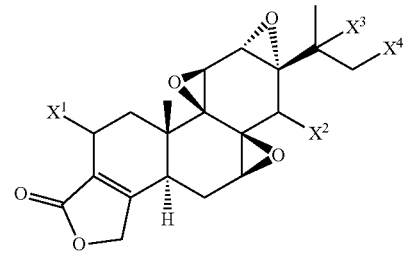

wherein
$X^1$ is H, $R^1$, OH or $OR^1$,
$X^2$ is H, $R^1$, OH, $OR^1$, =O or Y,
$X^3$ is H or OH,
$X^4$ is H, OH or $OR^1$,
$R^1$ is a $C_{1-4}$ alkyl group,
Y is $(CR^2R^3O)_nP(O)(O^-Z^+)_2$,
each $R^2$ is, independently, H, $C_{1-6}$ alkyl, aryl-$C_{1-6}$ alkyl-, $C_{3-6}$ cycloalkyl or aryl,
each $R^3$ is, independently, H, $C_{1-6}$ alkyl, aryl-$C_{1-6}$ alkyl-, $C_{3-6}$ cycloalkyl or aryl,
or $R^2$ and $R^3$, together with the carbon atom to which they are bonded form a $C_{3-7}$ cycloalkyl group,
wherein any alkyl or cycloalkyl group in $R^2$ or $R^3$ may be optionally substituted with one to five substituents selected from the group consisting of halo, $C_{1-6}$ alkoxy and $NR^aR^b$,
wherein any aryl group in $R^2$ or $R^3$ may be optionally substituted with one to five substituents selected from the group consisting of $C_{1-6}$ alkyl, $C_{1-6}$ alkoxy, $NR^aR^b$, nitro and cyano,
n is 1, 2 or 3,
each Z is H,
$R^a$ and $R^b$ are each, independently, H, $C_{1-6}$ alkyl, $C_{3-6}$ cycloalkyl or aryl,
or $R^a$ and $R^b$, together with the nitrogen atom to which they are bonded, form a pyrrolidino, piperidino, piperanino, azetidino, morpholino, or thiomorpholino group,
or a salt thereof.

In a preferred embodiment of the invention, $X^1$ is H, $CH_3$, OH or $OCH_3$.

In another preferred embodiment of the invention, $X^2$ is H, $CH_3$, OH, $OCH_3$ or =O.

In another preferred embodiment, $X^2$ is Y.

In another preferred embodiment of the invention, $X^3$ is H.

In another preferred embodiment of the invention, $X^4$ is H, OH or $OCH_3$.

In a preferred embodiment of the invention, (a) is triptolide, tripdiolide, 16-hydroxytriptolide, triptonide or minnelide.

In a particularly preferred embodiment, (a) is triptolide.

In a preferred embodiment of the invention, the organic diepoxide contains 8 to 14 carbon atoms.

In a preferred embodiment of the invention, the organic diepoxide contains two to four rings.

In a preferred embodiment of the invention, the organic diepoxide comprises at least one member selected from the group consisting of 4-vinylcyclohexene diepoxide (VCD), glycerol diglycidyl ether, 3,4-epoxy-cyclohexyl-methyl-3,4-epoxycyclohexyl carboxylate, 1,4-cyclohexanedimethanol diglycidyl ether, ethylene glycol diglycidyl ether, resorcinol glycidyl ether and 1,4-butanediol diglycidyl ether.

In a preferred embodiment of the invention, the organic diepoxide comprises 4-vinylcyclohexene diepoxide.

In a preferred embodiment of the invention, (a) is triptolide and (b) is 4-vinylcyclohexene diepoxide.

The present invention also includes a method of inducing ovarian follicle depletion in a female mammal, comprising administering an effective amount of the composition described above to the female mammal.

In a preferred embodiment of the invention, the mammal is a human or a non-human mammal.

The present invention also includes a method of reducing the reproductive capacity of a mammal, comprising administering an effective amount of the composition described above to the mammal.

In a preferred embodiment of the invention, the mammal is a female.

In a preferred embodiment of the invention, the mammal is a male.

In a preferred embodiment of the invention, the mammal is sterilized by administration of the composition.

The present invention also includes a method of controlling population size of a population of non-human mammals, comprising administering an effective amount of the composition described above to the population of non-human mammals.

The present invention also includes a method of inducing ovarian follicle depletion in a female mammal, comprising administering to the female mammal an effective amount of (a) a diterpenoid epoxide comprising a triptolide skeleton and which causes ovarian follicle depletion in female mammals, and (b) an organic diepoxide which causes ovarian follicle depletion in female mammals.

In one embodiment of the invention, (a) and (b) are administered as separate compositions.

The present invention also provides a method of reducing the reproductive capacity of a mammal, comprising administering to the mammal an effective amount of (a) a diterpenoid epoxide comprising a triptolide skeleton and which causes ovarian follicle depletion in female mammals, and (b) an organic diepoxide which causes ovarian follicle depletion in female mammals.

The present invention also provides a method of the controlling population size of a population of non-human mammals, comprising administering to the population of non-human mammals an effective amount of (a) a diterpenoid epoxide comprising a triptolide skeleton and which causes ovarian follicle depletion in female mammals, and (b) an organic diepoxide which causes ovarian follicle depletion in female mammals.

The present invention also provides a method of preparing the composition described above, comprising combining (a) and (b).

A more complete appreciation of the invention and many of the attendant advantages thereof will be readily obtained as the same becomes better understood by reference to the following Figures in conjunction with the detailed description below.

BRIEF DESCRIPTION OF THE FIGURES

The exemplary embodiments of the present invention will be described in connection with the appended drawing figures.

Figure 1:
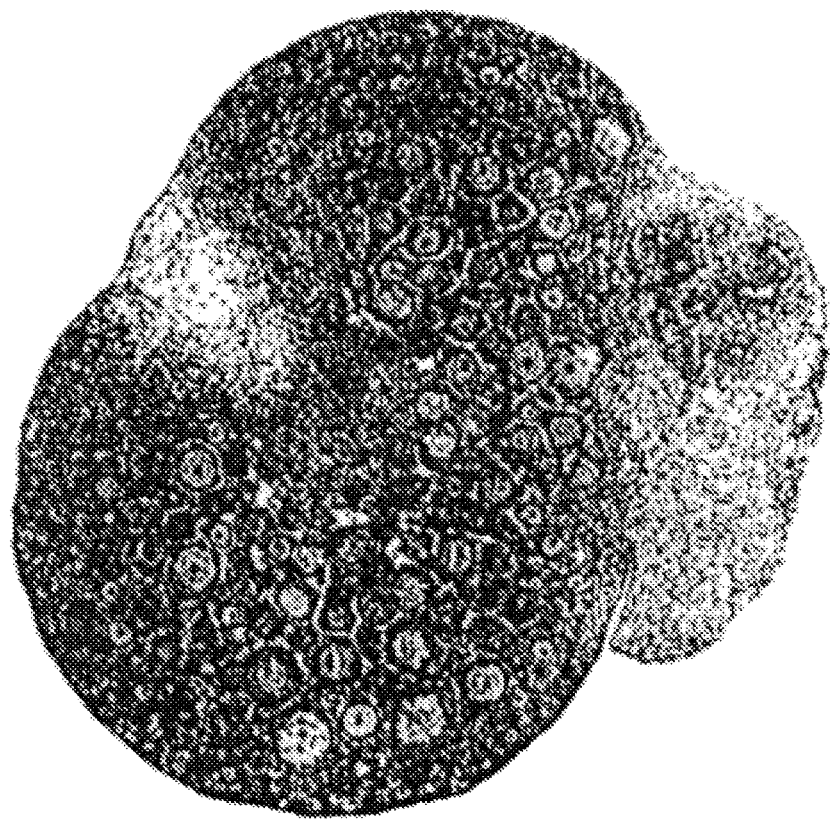
FIGS. 1 and 2 illustrate cultured control ovaries.

It will be appreciated that the figures are not necessarily drawn to scale. For example, the dimensions of some of the elements in the figures may be exaggerated relative to other elements to help to improve understanding of illustrated embodiments of the present invention.

DETAILED DESCRIPTION OF THE INVENTION

The present invention provides a composition suitable for depleting ovarian follicles in female mammals, comprising:

(a) a diterpenoid epoxide comprising a triptolide skeleton and which causes ovarian follicle depletion in female mammals when incorporated into the composition, i.e., used in combination with the epoxide (b), and (b) an organic diepoxide which causes ovarian follicle depletion in female mammals.

Triptolide is a well-known diterpenoid epoxide and many derivatives and analogs of this compound are also well-known and may be used in the present invention.

As a reference, the triptolide skeleton may be represented by the following structure:

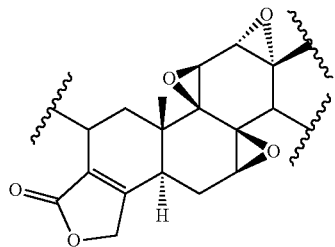 [SMILES: *C1C[C@@]2(C)[C@@H](C[C@@H]3O[C@@]34C(*)[C@@]3(*)O[C@H]3[C@@H]3O[C@]324)C2=C1C(=O)OC2]

Of course, compounds of the present invention have a variety of different substituents on the skeleton. Examples of such compounds are described below.

In a preferred embodiment of the invention, the diterpenoid epoxide comprising a triptolide skeleton (a) is represented by formula (I):

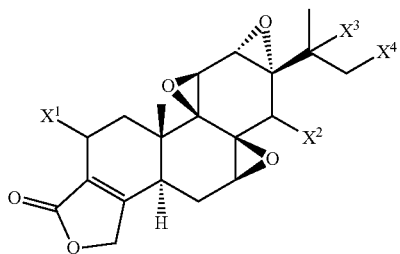

where
$X^1$ is H, $R^1$, OH or $OR^1$,
$X^2$ is H, $R^1$, OH, $OR^1$, =O or Y,
$X^3$ is H or OH,
$X^4$ is H, OH or $OR^1$,
$R^1$ is a $C_{1-4}$ alkyl group,
Y is $(CR^2R^3O)_nP(O)(O^-Z^+)_2$,
each $R^2$ is, independently, H, $C_{1-6}$ alkyl, aryl-$C_{1-6}$ alkyl-, $C_{3-6}$ cycloalkyl or aryl,
each $R^3$ is, independently, H, $C_{1-6}$ alkyl, aryl-$C_{1-6}$ alkyl-, $C_{3-6}$ cycloalkyl or aryl,
or $R^2$ and $R^3$, together with the carbon atom to which they are bonded form a $C_{3-7}$ cycloalkyl group,
wherein any alkyl or cycloalkyl group in $R^2$ or $R^3$ may be optionally substituted with one to five substituents selected from the group consisting of halo, $C_{1-6}$ alkoxy and $NR^aR^b$,
wherein any aryl group in $R^2$ or $R^3$ may be optionally substituted with one to five substituents selected from the group consisting of $C_{1-6}$ alkyl, $C_{1-6}$ alkoxy, $NR^aR^b$, nitro and cyano,
n is 1, 2 or 3,
each Z is H,
$R^a$ and $R^b$ are each, independently, H, $C_{1-6}$ alkyl, $C_{3-6}$ cycloalkyl or aryl,
or $R^a$ and $R^b$, together with the nitrogen atom to which they are bonded, form a pyrrolidino, piperidino, piperanino, azetidino, morpholino, or thiomorpholino group,
or a salt thereof.

In a preferred embodiment of the invention, $X^1$ is H, $CH_3$, OH or $OCH_3$.

In another preferred embodiment of the invention, $X^2$ is H, $CH_3$, OH, $OCH_3$ or =O.

In another preferred embodiment, $X^2$ is Y. In a particularly preferred embodiment of the invention, when $X^2$ is Y, then $X^1$, $X^3$ and $X^4$ are H.

In another preferred embodiment of the invention, $X^3$ is H.

In another preferred embodiment of the invention, $X^4$ is H, OH or $OCH_3$.

In a preferred embodiment of the invention, (a) is triptolide, tripdiolide, 16-hydroxytriptolide, triptonide or minnelide, including salts thereof.

In a particularly preferred embodiment, (a) is triptolide.

Detailed descriptions and methods of making compound (a) are provided in a variety of references, such as U.S. Pat. Nos. 6,294,546, 7,626,044, 6,548,537, 6,004,999, 8,268,882 and WO 2010/129918, each of which is incorporated herein by reference. Mixtures of different compounds within the scope of (a) are included in the present invention.

Component (b) of the inventive composition is an organic diepoxide which is capable of causing ovarian follicle depletion in female mammals. In a preferred embodiment of the invention, the organic diepoxide contains 8 to 14 carbon atoms. In another preferred embodiment of the invention, the organic diepoxide contains two to four rings, inclusive of the two epoxide rings.

In a preferred embodiment of the invention, the organic diepoxide comprises at least one member selected from the group consisting of 4-vinylcyclohexene diepoxide (VCD), glycerol diglycidyl ether, 3,4-epoxy-cyclohexyl-methyl-3,4-epoxycyclohexyl carboxylate, 1,4-cyclohexanedimethanol diglycidyl ether, ethylene glycol diglycidyl ether, resorcinol glycidyl ether and 1,4-butanediol diglycidyl ether. Mixtures of diexpoxides are within the scope of the invention.

Other organic diepoxides that may be used in the present invention include 1,2,3,4-diepoxybutane, 1,2,4,5-diepoxypentane, 1,2,5,6-diepoxypentane, 1,2,6,7-diepoxypentane, 1,2,7,8-diepoxyoctane, 1,2,3,4-diepoxycyclohexane, 1,2,5,6-diepoxycyclooctane, 9,10,12,13-diepoxystearic acid, 3,4-epoxy-6-methyl-cyclohexylmethyl-3,4-epoxy-6-methyl-cyclohexanecarboxylate, resorcinoldiglycidyl ether, hexaepoxyysqualene, bis-(2,3-epoxy-2-methylpropyl)ether, bis-(3,4-epoxybutyl)ether, ethylene glycol bis-(2,3-epoxy-2-methylpropyl)ether, 2,3-epoxy-2-ethylhexyl-9,10-epoxystearate, 2-ethyl-1,3-hexanediol bis-(9,10-epoxystearate), 2,3-bis(glycidyloxy)-1,4-dioxane, bis-(3,4-epoxycyclohexylmethyl) adipate, bis-(3,4-epoxy-methylcyclohexylmethyl) adipate, 3,4-epoxy-6-methylcyclohexylmethyl 3-4-epoxy-6-methylcyclohexanecarboxylate, limonene dioxide and bis-(2,3-epoxycyclopentyl) ether. Such compounds are described in, for example, Weil, *Industrial Hygiene Journal*, July-August 1963, pp. 305-325 and Van Duuren, *Annals New York Academy of Sciences*, 1969, pp. 633-651, both incorporated herein by reference.

In a preferred embodiment of the invention, the organic diepoxide comprises 4-vinylcyclohexene diepoxide. In a very particularly preferred embodiment of the invention, (a) is triptolide and (b) is 4-vinylcyclohexene diepoxide.

The chemical reactivity of the epoxides can determined in an alkylating assay using 4-(p-nitrobenzyl) pyridine (NBP) based on the method reported in "Detection of epoxides with 4-(p-nitrobenzyl) pyridine." Agarwal et. al. 1979, *Bull. Environm. Contam. Toxicol.* 23, 825-829, incorporated herein by reference.

The biological activity of the epoxides can be evaluated in an in vitro bioassay using rat pup ovaries based on method reported in "Characterization of a rat in vitro ovarian culture system to study the ovarian toxicant 4-vinylcyclohexene diepoxide." Devine et. al. 2002, *Toxicol. Appl. Pharmacol.*

184, 107-115, incorporated herein by reference. Biological activity can be determined by follicle counts in ovarian sections after week long culture with micro molar concentrations of the epoxide. In general, biologically active epoxides will also be chemically active as well but not vice versa.

The present invention also includes a method of inducing ovarian follicle depletion in a female mammal, comprising administering an effective amount of the composition described above to the female mammal.

In a preferred embodiment of the invention, the mammal is a human or a non-human mammal. Examples of non-human mammals include rodents (e.g., rats, mice, squirrels, prairie dogs, gophers, woodchucks, hamsters, nutria, beavers, voles), muskrats, cats, dogs, pigs, horses, cattle, coyotes, foxes, sheep, deer, goats, stoats, possums, opossums, rabbits, hares, kangaroos, wallabies, badgers, camels, elephants, burros, raccoons, bears, groundhogs, moles, bats and boars, for example.

The mammals listed above may be used in any embodiment of the invention described herein.

The present invention also includes a method of reducing the reproductive capacity of a mammal, comprising administering an effective amount of the composition described above to the mammal.

In a preferred embodiment of the invention, the mammal is a female. In another embodiment of the invention, the mammal is a male. It is noted that triptolide oral exposure is known to compromise male rat fertility to ultimate sterility. Thus, both male and females can be treated according to the present invention. In a preferred embodiment of the invention, the mammal is sterilized by the treatment in the present invention, i.e., the animal has lost its reproductive capacity.

The present invention also includes a method of controlling population size of a population of non-human mammals, comprising administering an effective amount of the composition described above to the population of non-human mammals. In this aspect of the invention, a number of animals, i.e., a population, are targeted for treatment over a range of area, e.g., in a park or wild-life preserve, agriculture, concentrated animal feeding operations, commercial businesses, residential, Federal lands. This embodiment of the invention is particularly useful in controlling the rodent (e.g., rat) population in an urban public transit system. For example, an urban subway system. New York City's subway system, for example, is well-known to have large rodent population. In this embodiment of the invention, the inventive composition is provided for the rodents to ingest throughout the system. Such a treatment is expected to reduce the size of the animal population, and possibly eliminate the population.

The present invention also includes all of the methods described above in which (a) and (b) are administered separately if desired, i.e., (a) and (b) are not incorporated into a single composition. In addition, while (a) and (b) will preferably administered at the same time, it is also within the scope of the present invention with respect to this embodiment that (a) and (b) can be administered at different times, with the understanding that both (a) and (b) will be present together to provide the synergistic effect provided by the present invention. Preferably, (a) and (b) are administered within 24, 12, 6, 3, 2 or 1 hour, or less, of each other.

In accordance with various embodiments, the composition of the present invention is configured to cause sterility in mammals by inducing ovarian depletion of follicles. According to various aspects of these embodiments, all stages of follicles are targeted. To cause permanent loss of ovarian function, the finite primordial pool of follicles is targeted. To cause rapid reduction in offspring production, growing follicles are targeted.

Component (b) of the present invention (e.g., VCD) is used to target primordial/primary follicles, and component (a) (e.g., triptolide) is used to target growing follicles. The combination is used to permanently suppress reproduction in the mammals so treated by the present invention. Additionally, triptolide is known to reduce fertility in male mammals, and so the composition reduces fertility in both male and female mammals. The composition can also be used to accelerate ovarian failure in mammals, such as peri-menopausal women.

A dose of an active agent may vary according to the purpose of treatment and type of animal. However, in accordance with exemplary embodiments of the disclosure, the composition includes about 1 mM to about 750 mM, or about 1 mM to about 500 mM, or about 10 mM to about 100 mM of (b) and about 1 nM to about 10 mM, or about 5 nM to about 1 mM, or about 5 nM to about 20 nM of (a). These ranges include all specific values and subranges therebetween, such as 10 nM, 25 nM, 50 nM, 100 nM, 250 nM, 500 nM, 5 mM, 25 nM, 50 mM and 250 mM. Surprisingly and unexpectedly, the compositions of the present invention were found to deplete all stages of ovarian follicles. The depletion is thought to result from the synergistic combination of (b) and (a), which is thought to allow for the use of lower concentrations of each of the agents, compared to compositions that do not include the combination, and which results in higher depletion percentages of follicles.

For in vitro culture applications, the molar ratio of (a) to (b) may range from 1/5 to 1/75,000, including all specific values and subranges therebetween, such as 1/10, 1/25, 1/50, 1/100, 1/250, 1/500, 1/1,000, 1/2,500, 1/5,000, 1/10,000, 1/25,000 and 1/50,000. For in vivo application (e.g., a bait), the corresponding molar ratio is generally 1/5 to 1/500, inclusive of all specific values and subranges therebetween, such as 1/10, 1/25, 1/50, 1/100 and 1/250.

For in vitro culture applications, the weight ratio of (a) to (b) generally ranges from 1/2 to 1/50,000, including all specific values and subranges therebetween, such as 1/10, 1/25, 1/50, 1/100, 1/250, 1/500, 1/1,000, 1/2,500, 1/5,000, 1/10,000 and 1/25,000. For in vivo application (e.g., a bait), the corresponding weight ratio is generally 1/5 to 1/500, inclusive of all specific values and subranges therebetween, such as 1/10, 1/25, 1/50, 1/100 and 1/250.

Although compositions including VCD were studied for inducing follicle depletion, it was found that VCD alone—as the only active ingredient—did not cause premature ovarian failure at low concentrations, or short exposure durations <15 days. Premature ovarian failure is when no more ovulations occur in spite of eggs/follicles being present in an ovary. For compositions and methods to function as a means of population control, the ovarian failure desirably occurs rapidly, for example within 10 days of treatment for rodents.

In accordance with various embodiments, a method of inducing ovarian follicle depletion includes the steps of providing a composition comprising VCD and triptolide, wherein the composition induces depletion of multiple stages of ovarian follicles. For example, the composition may cause depletion of primordial, secondary, and tertiary follicles and of corpora lutea. In accordance with further aspects, the combination may cause an increase in primordial follicle depletion and more complete destruction of the primordial follicles, compared to compositions including only VCD.

The composition and method disclosed herein can be used to sterilize various mammals (e.g., rodents, pigs, coyotes, dogs, cats, horses and the other animals described above), control the population of such animals, and the like by feeding the composition to mammal populations. As noted above, the composition reduces fertility in male mammals, so administering the composition to both males and females of a population is thought to further reduce the population, compared to compositions that only affect fertility of either males or females.

In accordance with additional embodiments, a non-human mammalian female having ovarian follicle depletion induced by the administration of a composition comprising VCD and triptolide, wherein the composition induces depletion of multiple stages of ovarian follicles, is provided. The animal may be used to, e.g., study menopause and post-menopausal treatments and may be used as an animal model for animals, such as humans.

The mammals may be fed in accordance with a variety of techniques, such as gavage and using bait. When gavage is used, the concentration of (b) (e.g., VCD) typically ranges from about 50 to about 200 mg/kg/day of the feed and the amount of (a) (e.g., triptolide) ranges from about 25 µg/kg body weight to about 100 µg/kg body weight of the composition. These ranges include all specific values and sub-ranges therebetween, including 35, 60, 75, 90, 125, 150 and 175 µg/kg body weight.

When bait is used, in accordance with exemplary embodiments, the bait is formulated, such that: the active ingredients consumed do not cause adverse side effects, bait takes occur in the presence of other food sources, the bait is environmentally neutral—i.e., the active ingredients do not persist in the environment and no residual tissue accumulation occurs, which could lead to secondary exposure of non-target animals, the active ingredients should not put humans at risk, and the bait production should be scalable for production. The bait may be solid, semisolid, or liquid.

Compositions in accordance with the present invention may include the ingredients described herein as well as additional and/or alternative inert materials, preservatives, and other constituents typically found in similar compositions. In the case where exemplary inert materials and/or preservatives are listed, these ingredients are merely exemplary, and it is understood that other similar ingredients may be substituted for the materials listed in the examples below.

EXAMPLES

Having generally described this invention, a further understanding can be obtained by reference to certain specific examples which are provided herein for purposes of illustration only and are not intended to be limiting unless otherwise specified.
In Vitro Comparative Example 1

Figure 2:
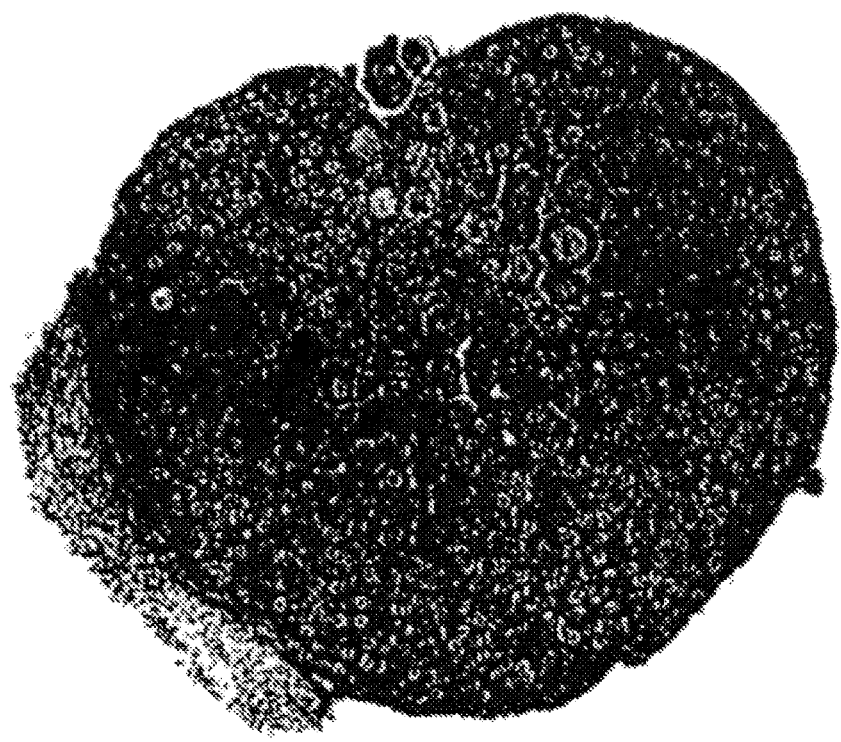

FIGS. 1 and 2 illustrate images of 4 day old rat pup ovaries. The control ovaries illustrate abundant primordial/primary and developing secondary follicles.

Comparative Example 2

Figure 3A:
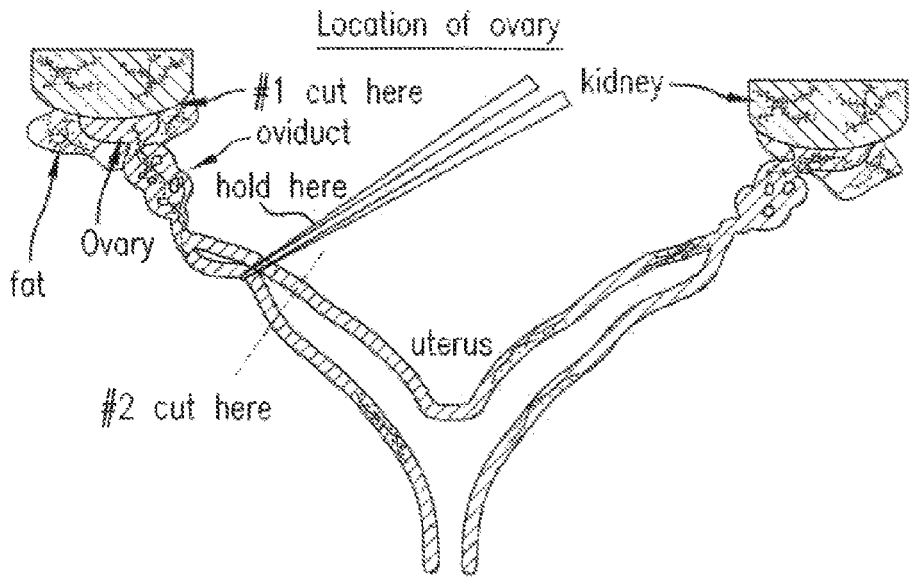
FIG. 3 illustrates an in vitro culture system. A. Collection of ovary from postnatal day 4 rat pup. B. Trim excess tissue from ovary under a dissecting microscope. C. Isolated ovary is placed on membrane floated on medium.
Figure 3B:
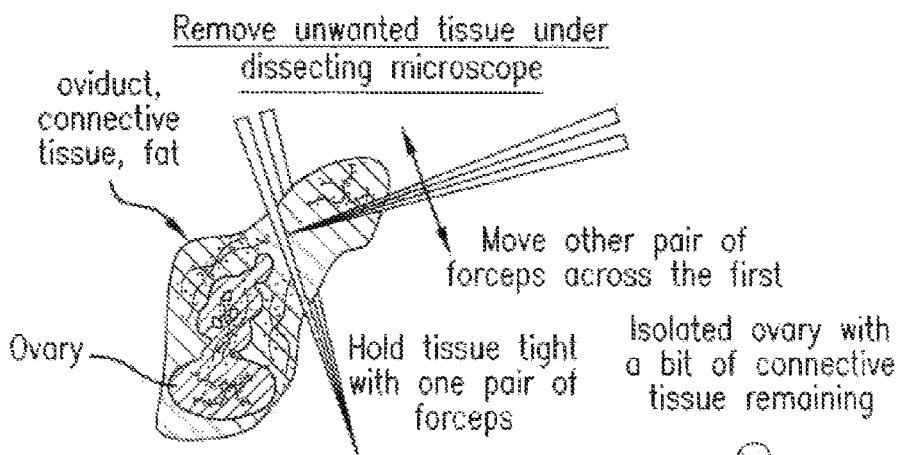
Figure 3C:
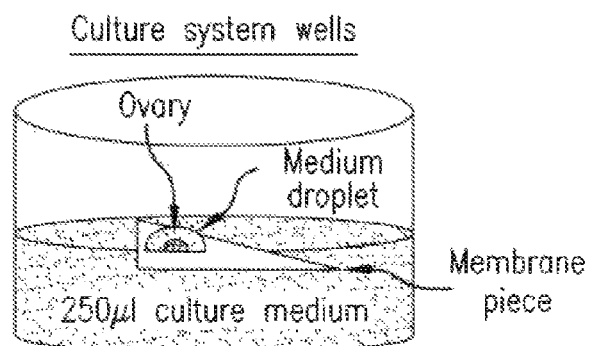

FIG. 3 illustrates an in vitro culture system for evaluating the efficacy of follicle-depletion compositions (developed by Patrick J. Devine). As set forth in the various examples herein, ovaries are cultured with VCD with or without triptolide in serum-free media for 8 days, no gonadotropins present, no media changes and active ingredients added just once at start of culture. Ovaries are collected and processed for histology to perform follicle counting.

Figure 4:
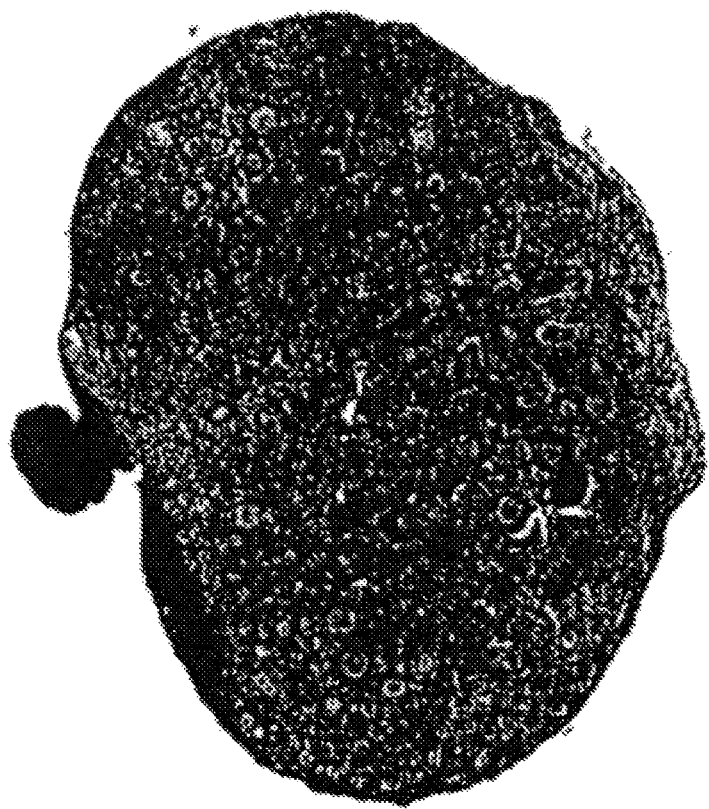
FIG. 4 illustrates a cultured ovary treated with 30 μm VCD.

FIG. 4 illustrates an ovary treated with 30 µm VCD. As illustrated, the ovary exhibited a 38% reduction in primordial follicles. The other stages of follicles were not significantly affected by the treatment.

Example 3

Figure 5:
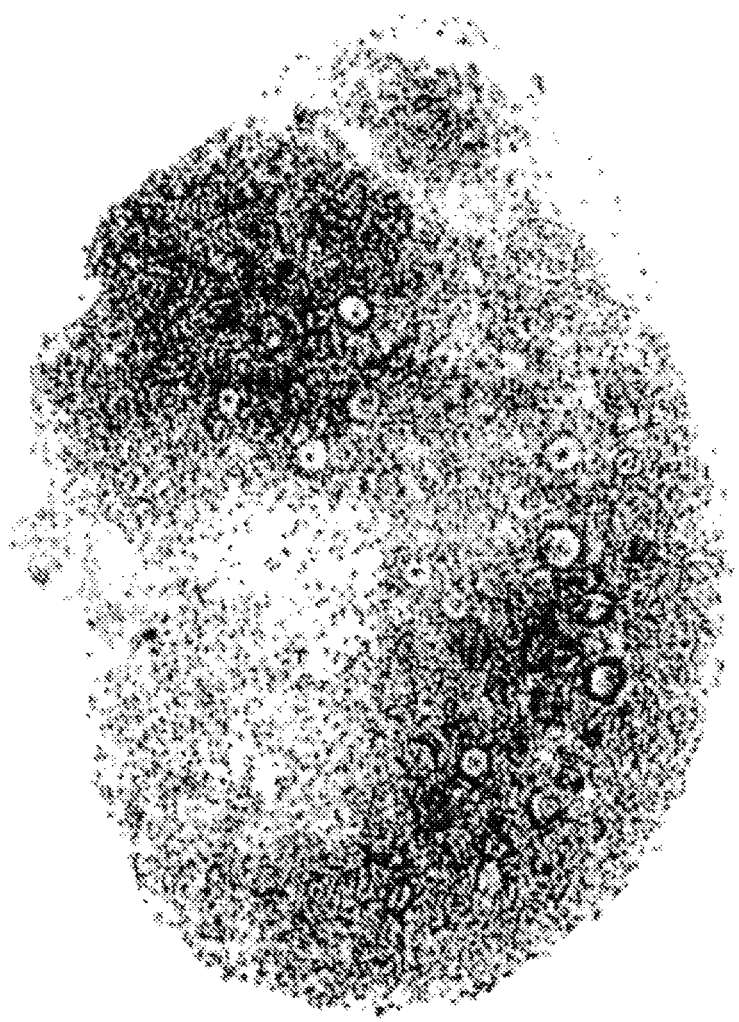
FIG. 5 illustrates a cultured ovary treated with 30 μm VCD and 5 nm triptolide.

FIG. 5 illustrates a cultured ovary treated with 30 µm VCD and 5 nm triptolide using the system and method of comparative example 2. The ovary has no apparent healthy follicles and exhibits extensive atresia and pyknosis. As illustrated, in vitro application of the composition to the ovary caused 100% depletion of all stages of follicles.

Example 4

Figure 6:
FIG. 6 illustrates a cultured ovary treated with 30 μm VCD and 10 nm triptolide.

FIG. 6 illustrates a cultured ovary treated with 30 µm VCD and 10 nm triptolide. As illustrated, in vitro application of the composition to the ovary caused 100% depletion of all stages of follicles.
In Vivo Example 5

In vivo studies were performed using a 15-day feeding trial of juvenile female Sprague-Dawley rats. The VCD concentration was held constant at 75 mM and the triptolide concentration was varied as noted below. The Experiment design was as follows:
  Control no active ingredients (n=6)
  VCD+triptolide 25 µg/kg body weight (n=7)
  VCD+triptolide 50 µg/kg body weight (n=7)
  VCD+triptolide 100 µg/kg body weight (n=7)

Figure 7:
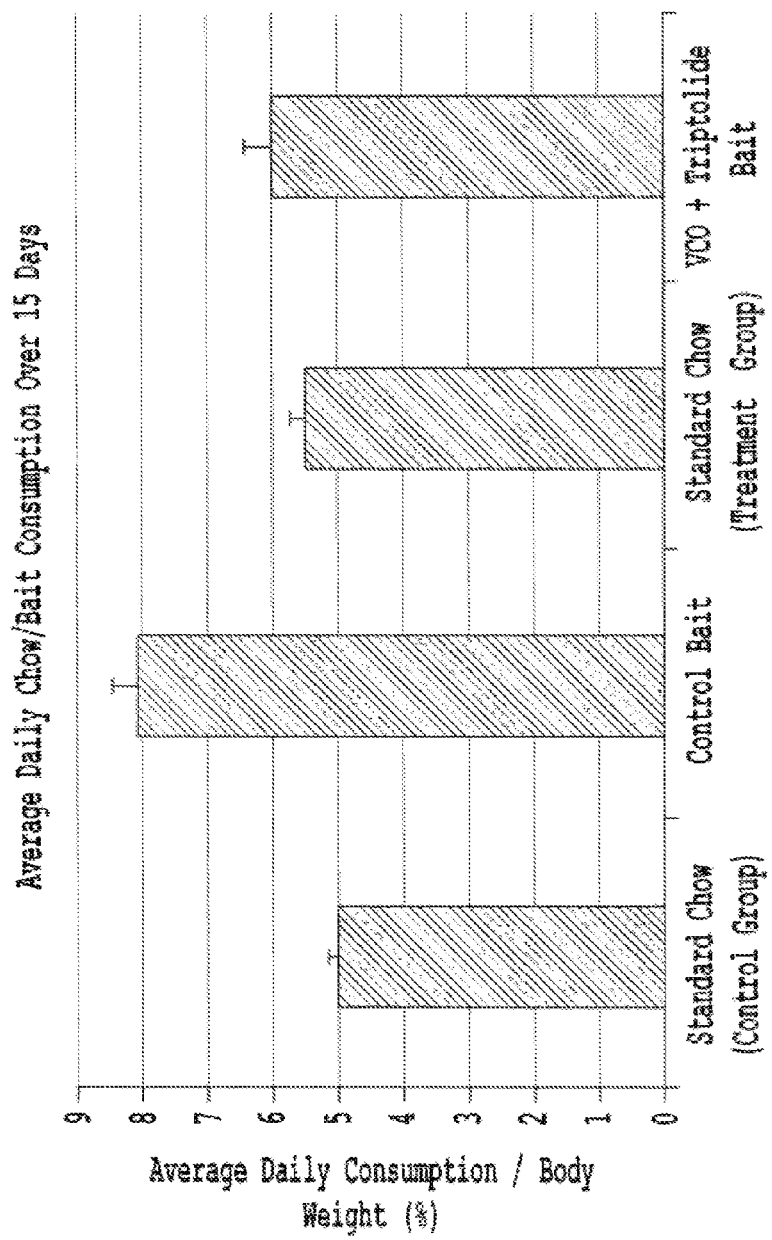
FIG. 7 illustrates chow/bait consumption of study rats.
Figure 8:
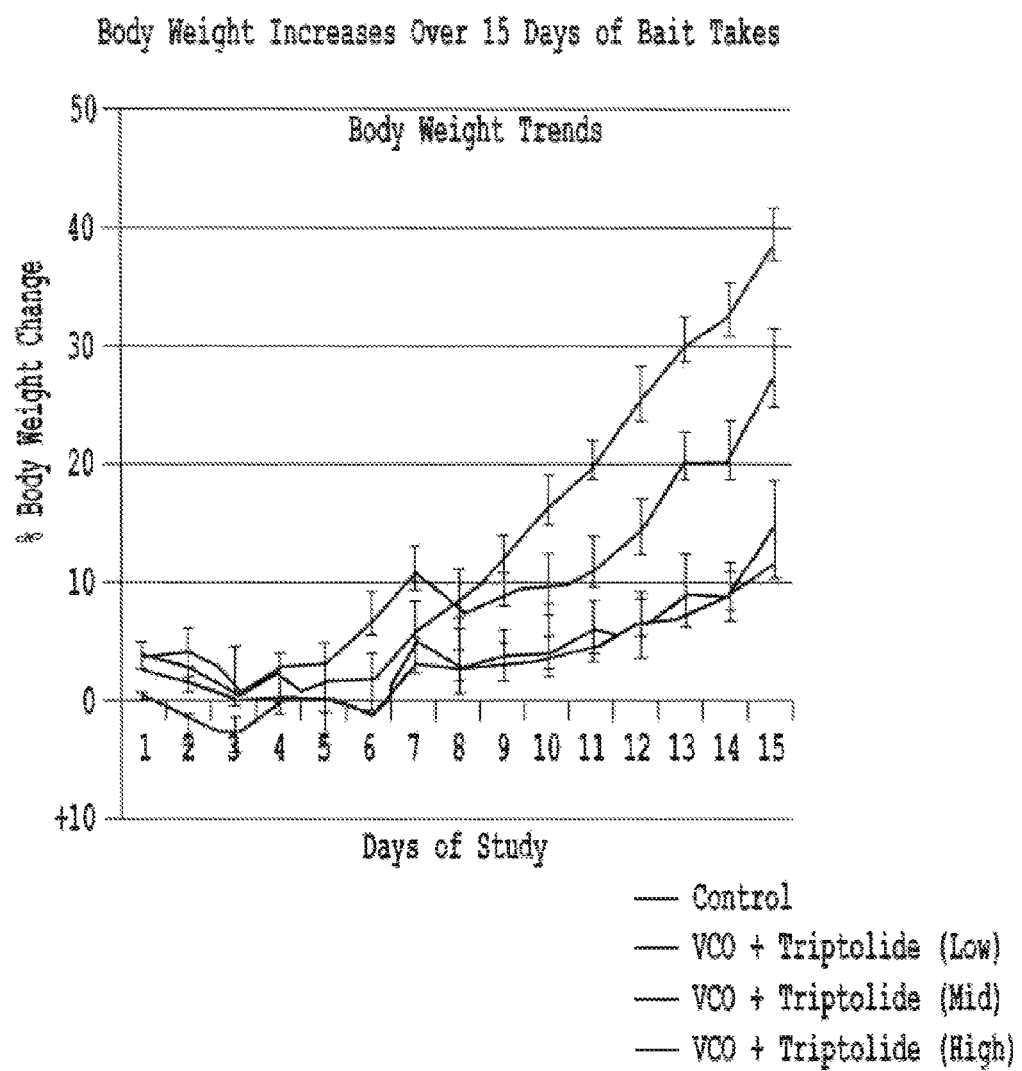
FIG. 8 illustrates body weight increase of the study rats.
Figure 9A:
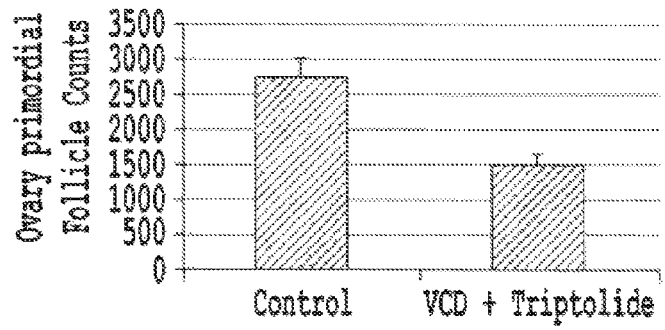
FIG. 9 illustrates follicle counts of rats fed bait containing VCD and triptolide.
Figure 9B:
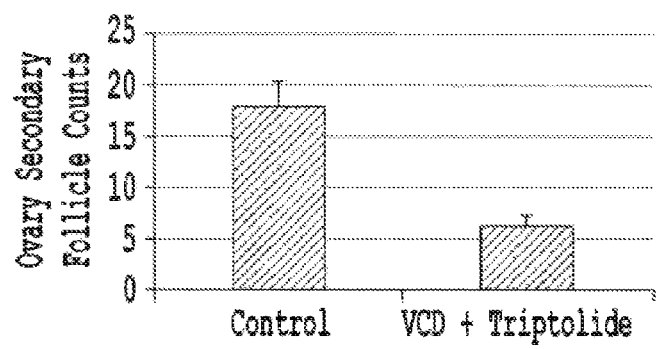
Figure 9C:
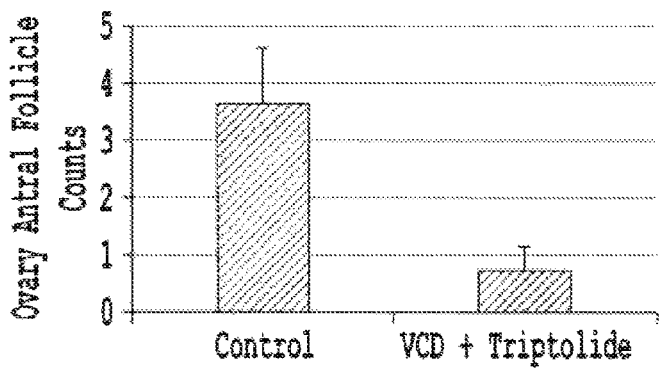
Figure 9D:
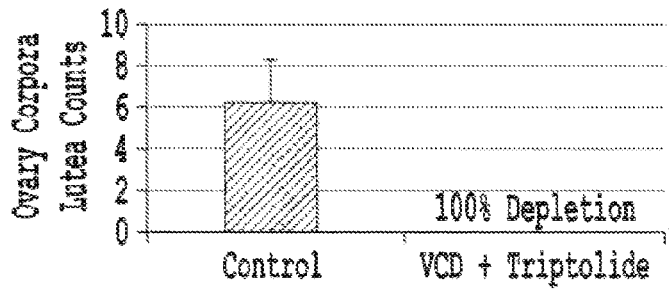

The experiment was designed to assess: palatability and quantity of bait consumed, health of rats (body weight recorded daily), and ovaries collected for follicular analysis. The rats had access to standard chow along with the control or treatment bait for 15 consecutive days. FIG. 7 illustrates the average daily consumption/body weight for each group and FIG. 8 illustrates body weight trends for each group.

Figure 10:
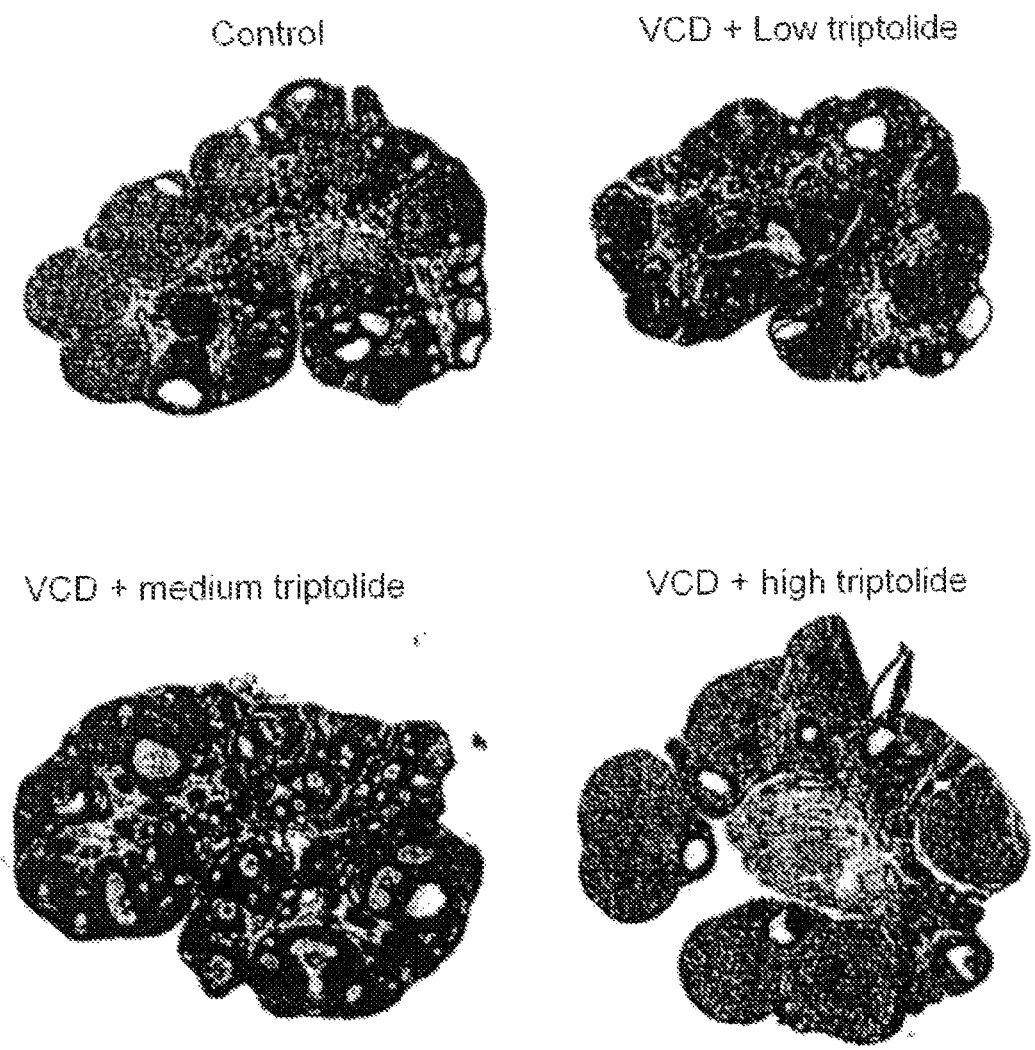
FIG. 10 illustrates ovarian images of ovaries of rates fed bait containing VCD and triptolide.
Figure 11:
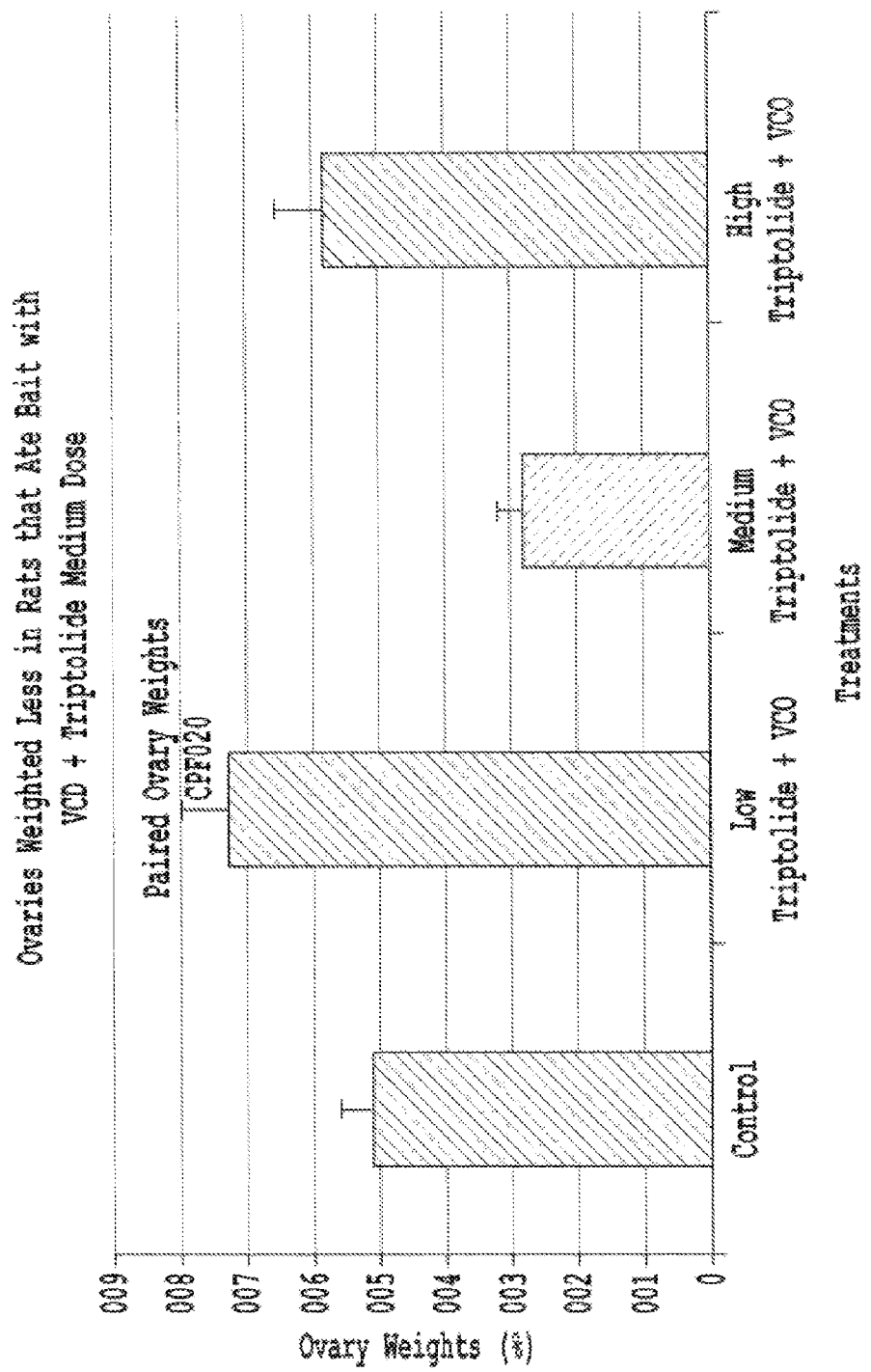
FIG. 11 illustrates ovary weights of study rats.

FIG. 9 illustrates primordial follicle counts, secondary follicle counts, antral follicle counts, and corpus lutea counts for each of the groups. Compared to the control group, the group treated with triptolide 50 µg/kg body weight exhibited 50% depletion in primordial follicle counts, 64% depletion in secondary follicle counts, 80% depletion in antral follicle counts, and 100% depletion in corpora lutea counts. FIG. 10 illustrates images of ovaries from each group and FIG. 11 illustrates ovary weights for each group.
Efficacy In Vivo A bait composition containing two active ingredients, 4-vinylcyclohexene diepoxide at 0.099% by weight and triptolide at 0.0012% was provided to immature Sprague Dawley female rats for 15 successive nights in the presence of unlimited water and laboratory rat chow and they consumed >10% of their body weight/night. The next day after the end of dosing the female rats were bred for 21 days with untreated, proven adult male breeders. The control rats that consumed an emulsion without active ingredients gave birth to average litters of 12.2 rat pups after an average of 39.7 days from the start of dosing. The rats that consumed the inventive bait composition had an average litter size of 4.3 pups after an average of 55.9 days from the start of dosing.

However, 2 of the 8 rats that drank the inventive composition never delivered a litter and another 2 rats delivered a litter of 1 pup.

Additionally in the group fed the inventive bait, the rat that consumed the least amount of all 8 rats, 8 mg/kg body weight versus 16 mg/kg body weight for the other 7 rats, gave birth to a litter of 15 pups-clearly indicating an inverse dose response relationship between composition consumed and number of pups/litter. These results are consistent with the data presented above which were reduced follicle counts after consumption of the inventive bait. In that data set there was a more pronounced effect of bait on growing follicles and corpora lutea suggesting there were fewer ovulations. Therefore, consumption of the composition of the present invention by female rats reduced ovarian ovulations to the extent that there are 65% fewer pups produced and the delayed ovulations significantly extend the time to delivery. Combining these two effects in rats that have short lives, less than 1 year in the wild, exerts a profound effect on the total of number of rat pups born per female rat and ultimately the overall population size.

Example 6

In Vivo Application of a Bait Composition

Bait compositions with a constant concentration of VCD and increasing triptolide concentrations were prepared.

Figure 12A:
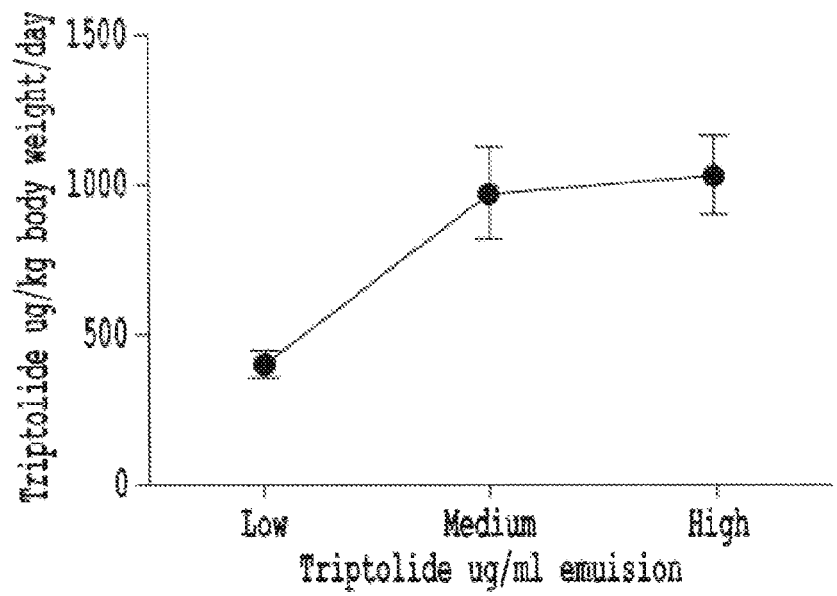
FIG. 12: Illustrates the results of immature female rats consuming bait with constant VCD (0.099% concentration) combined with increasing triptolide concentrations.
Figure 12B:
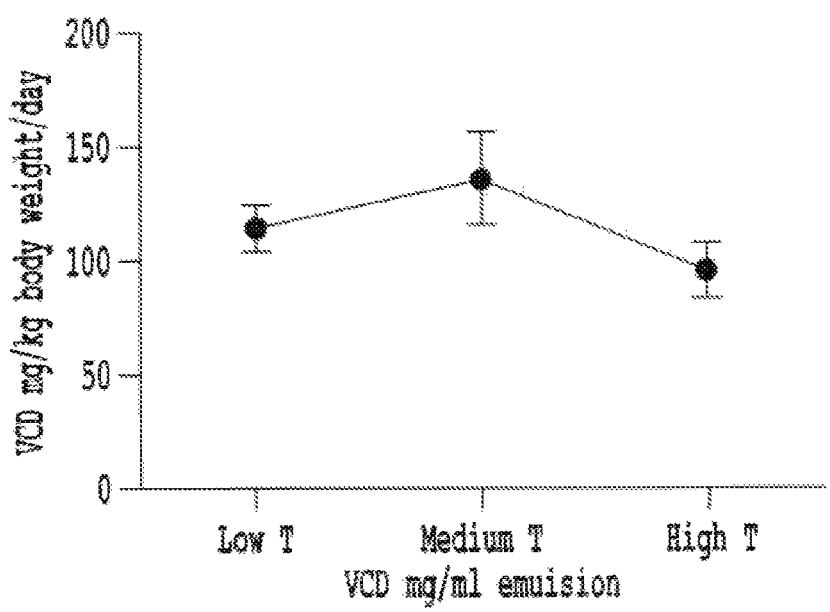

Immature female rats consumed bait with constant VCD (0.099% concentration) combined with increasing triptolide concentrations, low 3.99 µg/ml, medium 7.96 µg/ml, and high 11.92 µg/ml for 15 days. FIG. 12A is the amount of triptolide consumed per day of low, medium, high dose groups mean±SEM. FIG. 12B is the amount of VCD consumed per day of low, medium, high triptolide dose groups mean±SEM.

Figure 13:
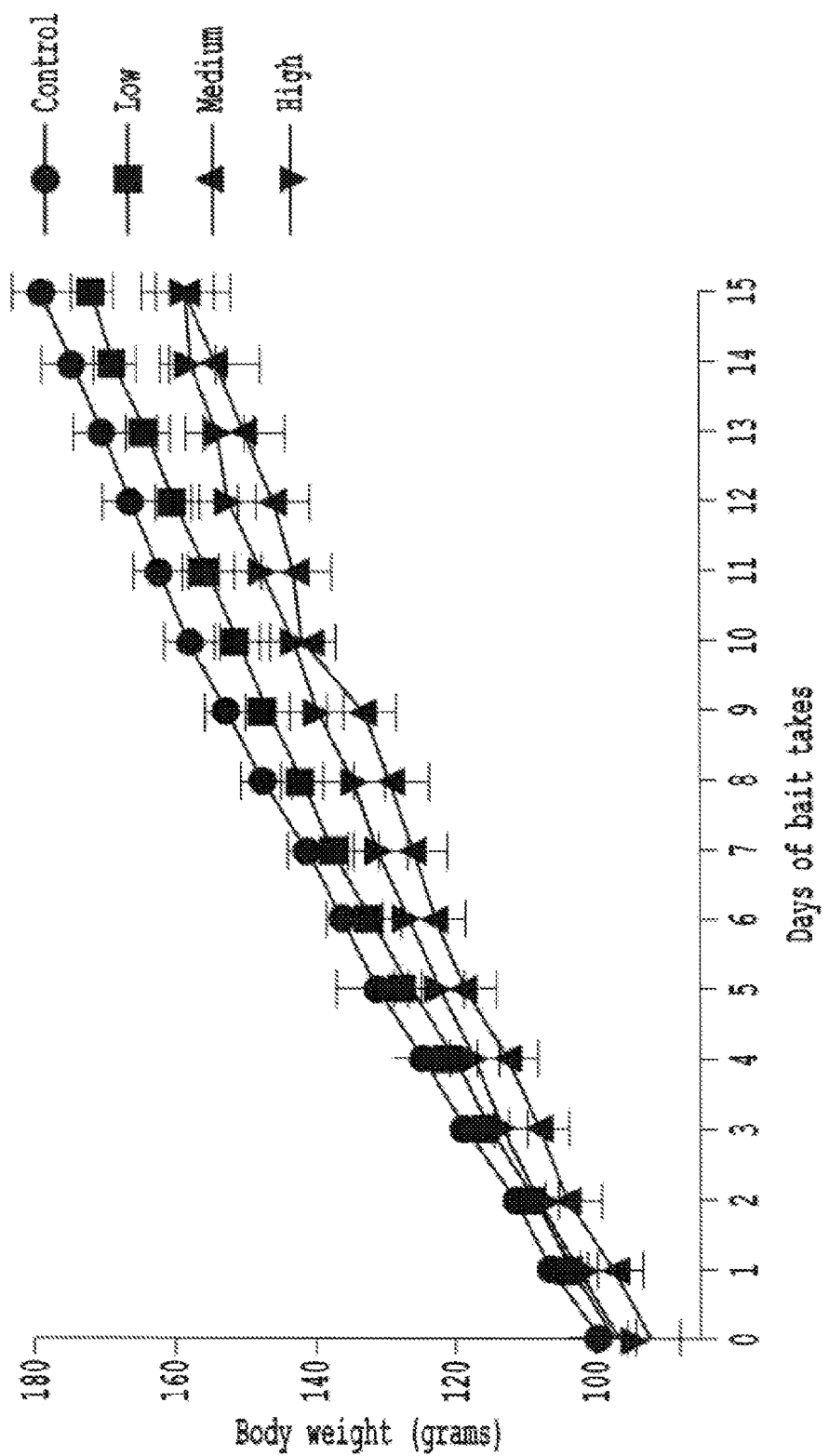
FIG. 13: Illustrates the results of immature female rats consuming unlimited chow and water during entire treatment period.

Immature female rats had unlimited chow and water during entire treatment period. Day 0 represents the first night of having bait with active ingredients triptolide and VCD presented during lights off time period. The next morning the amount of bait consumed was measured and the rats were assessed for general health and weighed. The results are shown in FIG. 13. The data presented in FIG. 13 shows that during the time the rats were eating the bait they continued to grow at similar rates. In addition, the rats' general condition was good and they ate the bait at a constant amount during the entire 15 days, about 8%-10% of their body weight.

Figure 14:
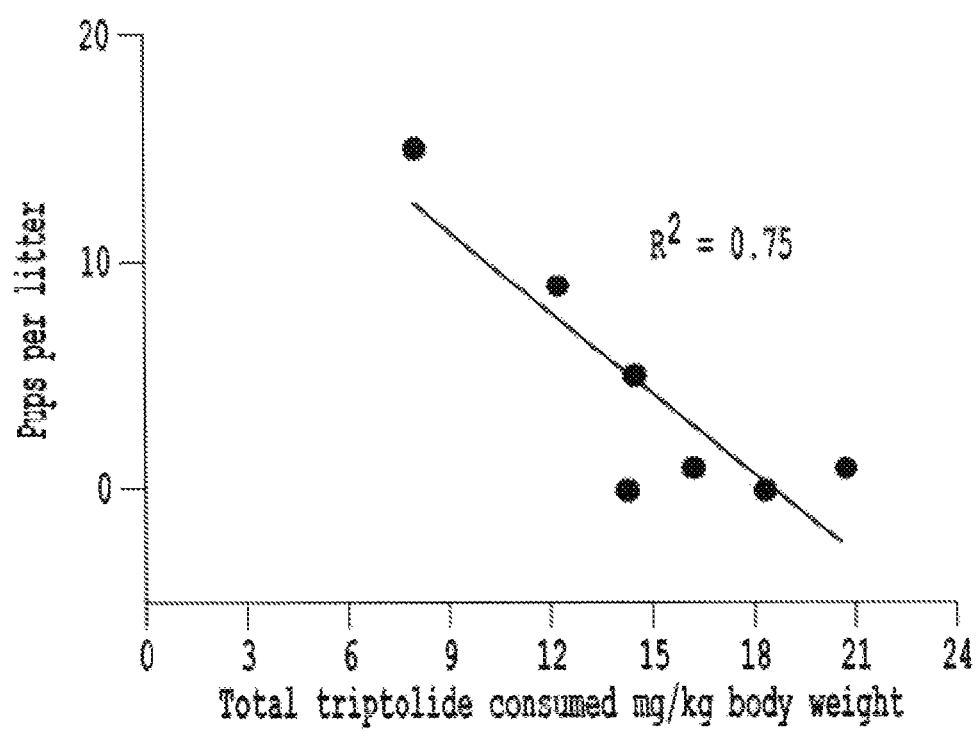
FIG. 14: Illustrates that the effect on pups born per litter was dose dependent on triptolide. The x-axis denotes total triptolide consumed mg/kg body weight.

Immature female rats ate bait with high triptolide concentration and VCD at 0.099% for 15 days. The day after the last bait take the female rats were bred with untreated, proven male breeder rats. Number of pups per litter were counted at post natal day 4. The results are shown in FIG. 14. The data presented in FIG. 14 shows that the effect on pups born per litter was dose dependent on triptolide. There is a strong inverse correlation between amount of triptolide dose and number of pups born per litter.

Figure 15:
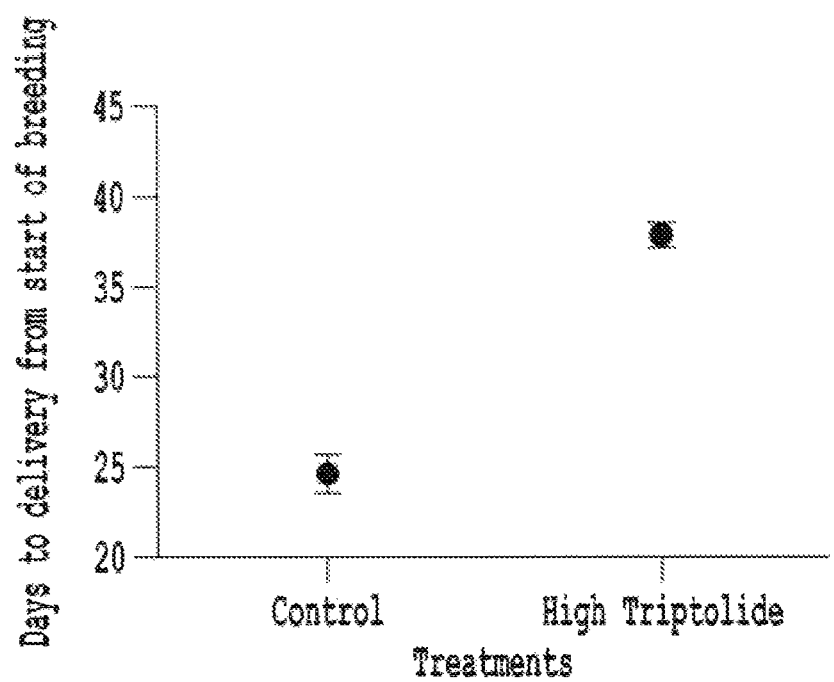
FIG. 15: Illustrates the results of immature female rats consuming control bait, no active ingredients, and treated females eating bait with VCD at 0.099% and high dose of triptolide for 15 days.
Figure 16:
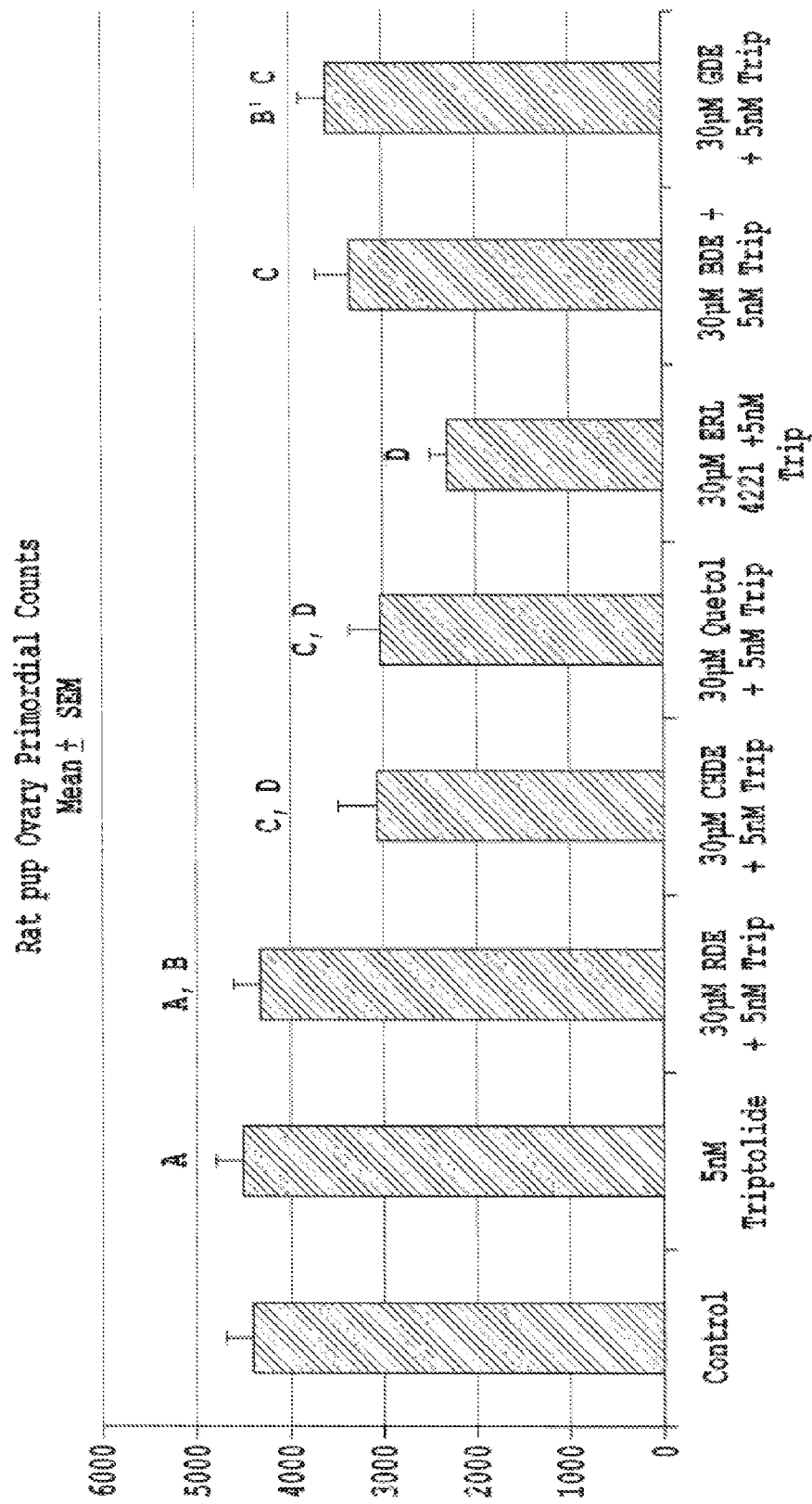
FIG. 16: Illustrates the results of an in vitro bioassay of follicle depletion.

Immature female rats ate control bait, no active ingredients, and treated females ate bait with VCD at 0.099% and high dose of triptolide for 15 days. The day after end of baiting the treated female rats were bred with proven male breeder rats. Days to delivery were counted from day 0 of breeding to parturition. The data is presented in FIG. 15, where symbols are mean for each group±SEM.

Example 7

In Vitro Assay

In vitro bioassay of follicle depletion, ovaries cultured for 8 days with different chemicals Control—no chemicals, Triptolide—5 nM (Trip), Diepoxides, RDE, CHDE, Quetol, ERL 4221, BDE, GDE, each at 30 µM+Trip 5 nM Ovaries were prepared for histological analysis for determination of follicle depletion Compared chemical (reactivity in epoxide assay) to biological activity (follicle depletion)

| Chemical reactivity | Diepoxide | Biological activity |
| --- | --- | --- |
| 4 | RDE | 1 |
| 5 | GDE | 2 |
| 6 | BDE | 3 |
| 3 | CHDE | 4 |
| 2 | Quetol | 5 |
| 1 | ERL 42221 | 6 |

Ranking, 1—least chemical reactivity/biological activity, 6—most chemical reactivity/biological activity Conclusions 1. In a previous experiment none of these diepoxides tested at 30 µM caused significant follicle depletion.
2. In this experiment, Triptolide (Trip) at 5 nM did not cause significant follicle depletion.
3. Only when Triptolide and GDE, BDE, CHDE, Quetol and ERL 4221 were combined was there significant follicle depletion. Triptolide+RDE combination did not cause significant follicle depletion.
4. ERL 4221 is best illustration of relationship between chemical and biological activity. ERL 4221 was least chemically reactive while being most biologically active when combined with Trip.
5. The combination of Trip and these diepoxides GDE, BDE, CHDE, Quetol, ERL 4221 caused significant follicle depletion apparently via synergistic interactions.

The present invention has been described above with reference to a number of exemplary embodiments and examples. It should be appreciated that the particular embodiments shown and described herein are illustrative of the preferred embodiments of the invention and its best mode, and are not intended to limit the scope of the invention as set forth in the claims. It will be recognized that changes and modifications may be made to the embodiments described herein without departing from the scope of the present invention. These and other changes or modifications are intended to be included within the scope of the present invention, as expressed in the following claims and the legal equivalents thereof Obviously, numerous modifications and variations of the present invention are possible in light of the above teachings. It is therefore to be understood that within the scope of the appended claims, the invention may be practiced otherwise than as specifically described herein.

The invention claimed is:
1. A composition, comprising:
(a) triptolide, and
(b) 4-vinylcyclohexene diepoxide (VCD),
wherein the composition is in the form of an edible bait
that can be consumed by the male and female rats and wherein (a) and (b) are present in an amount to synergistically reduce the reproductive capacity of the male and female rats while not otherwise negatively effecting general health of the male and female rats.

2. The composition of claim 1, wherein the concentration of (a) in the composition is about 1 nM to about 10 mM and the concentration of (b) in the composition is about 1 mM to about 750 nM.

3. The composition of claim 1, wherein the molar ratio of (a) to (b) is from 1/5 to 1/75,000.

4. The composition of claim 1, wherein the weight ratio of (a) to (b) is 1/2 to 1/50,000.

5. The composition of claim 1, wherein the weight ratio of (a) to (b) is 1/5 to 1/500.

6. A method of reducing the reproductive capacity of a population of rats, comprising feeding a population of rats comprising male and female rats with an effective amount of the composition of claim 1, wherein
the composition is consumed by both the male and the female rats, and
the composition reduces the reproductive capacity of both the male and the female rats.

7. A method of reducing the reproductive capacity of a population of rats, comprising feeding a population of rats comprising male and female rats with an effective amount of the composition of claim 2, wherein
the composition is consumed by both the male and the female rats, and
the composition reduces the reproductive capacity of both the male and the female rats.

8. A method of reducing the reproductive capacity of a population of rats, comprising feeding a population of rats comprising male and female rats with an effective amount of the composition of claim 3, wherein
the composition is consumed by both the male and the female rats, and
the composition reduces the reproductive capacity of both the male and the female rats.

9. A method of reducing the reproductive capacity of a population of rats, comprising feeding a population of rats comprising male and female rats with an effective amount of the composition of claim 4, wherein
the composition is consumed by both the male and the female rats, and
the composition reduces the reproductive capacity of both the male and the female rats.

10. A method of reducing the reproductive capacity of a population of rats, comprising feeding a population of rats comprising male and female rats with an effective amount of the composition of claim 5, wherein
the composition is consumed by both the male and the female rats, and
the composition reduces the reproductive capacity of both the male and the female rats.

11. A method of reducing the reproductive capacity of a male rat, comprising administering an effective amount of the composition of claim 1 to the male rat.

12. A method of reducing the reproductive capacity of a male rat, comprising administering an effective amount of the composition of claim 2 to the male rat.

13. A method of reducing the reproductive capacity of a male rat, comprising administering an effective amount of the composition of claim 3 to the male rat.

14. A method of reducing the reproductive capacity of a male rat, comprising administering an effective amount of the composition of claim 4 to the male rat.

15. A method of reducing the reproductive capacity of a male rat, comprising administering an effective amount of the composition of claim 5 to the male rat.

16. The composition of claim 1, which is in the form of a solid or semisolid.

17. The composition of claim 1, which is in the form of a liquid.

* * * * *